(12) United States Patent
Biedermann et al.

(10) Patent No.: US 9,907,578 B2
(45) Date of Patent: *Mar. 6, 2018

(54) BONE ANCHORING ELEMENT AND STABILIZATION DEVICE FOR BONES, IN PARTICULAR FOR THE SPINAL COLUMN

(71) Applicant: Biedermann Technologies GmbH & Co. KG, Donaueschingen (DE)

(72) Inventors: Lutz Biedermann, VS-Villingen (DE); Jürgen Harms, Karlsruhe (DE); Helmar Rapp, Deißlingen (DE); Berthold Dannecker, St. Georgen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/798,072

(22) Filed: Jul. 13, 2015

(65) Prior Publication Data

US 2016/0008035 A1   Jan. 14, 2016

Related U.S. Application Data

(63) Continuation of application No. 12/550,654, filed on Aug. 31, 2009, now Pat. No. 9,101,403.

(Continued)

(30) Foreign Application Priority Data

Sep. 5, 2008   (EP) ..................... 08015721

(51) Int. Cl.
*A61B 17/70*   (2006.01)
*A61B 17/56*   (2006.01)

(52) U.S. Cl.
CPC ...... *A61B 17/7037* (2013.01); *A61B 17/7032* (2013.01); *A61B 17/701* (2013.01);
(Continued)

(58) Field of Classification Search
CPC .................. A61B 17/70–17/7008; A61B 17/7019–17/7034; A61B 17/8605
(Continued)

(56) References Cited

U.S. PATENT DOCUMENTS 3,865,105 A * 2/1975 Lode ................. A61B 17/7049
606/250
3,997,138 A * 12/1976 Crock ............... A61B 17/7001
248/67.5

(Continued)

FOREIGN PATENT DOCUMENTS

CA   2 577 436 A1   6/2006
DE   101 17 426 A1   10/2002
(Continued)

OTHER PUBLICATIONS

European Search Report dated Nov. 20, 2008 for European Application No. 08015721.7, Applicant Biedermann Motech GmbH, European Search Report dated Dec. 9, 2008 (9 pgs.).

*Primary Examiner* — Eduardo C Robert
*Assistant Examiner* — Michelle C Eckman
(74) *Attorney, Agent, or Firm* — Lewis Roca Rothgerber Christie LLP

(57) ABSTRACT

A bone anchoring element includes an anchoring section for anchoring in the bone and a receiving part connected to the anchoring section. The receiving part includes an opening suitable for accommodation of a stabilization rod having a rod axis, the opening being limited along the rod axis by two (Continued)

side walls. The side walls include guides orientated along the rod axis for guiding at least one connection rod therethrough.

15 Claims, 9 Drawing Sheets

Related U.S. Application Data

(60) Provisional application No. 61/094,664, filed on Sep. 5, 2008.

(52) U.S. Cl.
CPC ....... *A61B 17/7011* (2013.01); *A61B 17/7028* (2013.01); *A61B 17/7041* (2013.01); *A61B 2017/564* (2013.01)

(58) Field of Classification Search
USPC ............... 606/246, 254–255, 257, 259–261, 606/264–278
See application file for complete search history.

(56) References Cited

U.S. PATENT DOCUMENTS

| | | | |
|---|---|---|---|
| 4,653,481 A * | 3/1987 | Howland | A61B 17/7001 248/67.5 |
| 4,697,582 A * | 10/1987 | William | A61B 17/7041 606/254 |
| 4,805,602 A * | 2/1989 | Puno | A61B 17/7032 24/135 N |
| 5,133,717 A * | 7/1992 | Chopin | A61B 17/7055 606/264 |
| 5,147,360 A * | 9/1992 | Dubousset | A61B 17/705 606/250 |
| 5,152,303 A * | 10/1992 | Allen | A61B 17/7049 128/898 |
| 5,261,911 A * | 11/1993 | Carl | A61B 17/7049 606/250 |
| 5,312,402 A * | 5/1994 | Schlapfer | A61B 17/645 606/267 |
| 5,330,473 A * | 7/1994 | Howland | A61B 17/705 403/396 |
| 5,368,594 A * | 11/1994 | Martin | F16B 2/12 128/899 |
| 5,374,267 A * | 12/1994 | Siegal | A61B 17/7056 606/250 |
| 5,387,212 A * | 2/1995 | Yuan | A61B 17/701 606/264 |
| 5,437,669 A * | 8/1995 | Yuan | A61B 17/7047 606/264 |
| 5,454,812 A * | 10/1995 | Lin | A61B 17/7022 606/252 |
| 5,466,238 A * | 11/1995 | Lin | A61B 17/7008 606/264 |
| 5,470,333 A * | 11/1995 | Ray | A61B 17/7055 606/261 |
| 5,474,551 A * | 12/1995 | Finn | A61B 17/7041 606/264 |
| 5,499,983 A * | 3/1996 | Hughes | A61B 17/701 403/298 |
| 5,507,746 A * | 4/1996 | Lin | A61B 17/7041 403/400 |
| 5,611,801 A * | 3/1997 | Songer | A61B 17/82 606/103 |
| 5,702,393 A * | 12/1997 | Pfaifer | A61B 17/7049 606/250 |
| 5,702,394 A * | 12/1997 | Henry | A61B 17/7049 606/265 |
| 5,702,395 A * | 12/1997 | Hopf | A61B 17/7044 606/250 |
| 5,746,741 A * | 5/1998 | Kraus | A61B 17/171 606/267 |
| 5,800,435 A * | 9/1998 | Errico | A61B 17/7007 606/261 |
| 5,810,817 A * | 9/1998 | Roussouly | A61B 17/7041 606/250 |
| 5,863,293 A * | 1/1999 | Richelsoph | A61B 17/7037 606/271 |
| 5,899,903 A * | 5/1999 | Cotrel | A61B 17/7049 606/276 |
| 5,993,449 A * | 11/1999 | Schlapfer | A61B 17/7059 606/60 |
| 6,086,590 A * | 7/2000 | Margulies | A61B 17/7053 606/263 |
| 6,136,000 A * | 10/2000 | Louis | A61B 17/7047 606/250 |
| 6,136,002 A * | 10/2000 | Shih | A61B 17/7044 606/250 |
| 6,146,386 A * | 11/2000 | Blackman | A61B 17/7079 606/103 |
| 6,176,861 B1 * | 1/2001 | Bernstein | A61B 17/7007 606/246 |
| 6,206,879 B1 * | 3/2001 | Marnay | A61B 17/7035 606/53 |
| 6,254,603 B1 * | 7/2001 | Gertzbein | A61B 17/7041 606/250 |
| 6,287,311 B1 * | 9/2001 | Sherman | A61B 17/7032 411/909 |
| 6,315,779 B1 * | 11/2001 | Morrison | A61B 17/7007 606/269 |
| 6,368,320 B1 * | 4/2002 | Le Couedic | A61B 17/7049 606/246 |
| 6,432,140 B1 * | 8/2002 | Lin | A61B 17/70 606/247 |
| 6,471,706 B1 * | 10/2002 | Schumacher | A61B 17/66 606/281 |
| 6,565,569 B1 * | 5/2003 | Assaker | A61B 17/7037 606/250 |
| 6,645,207 B2 | 11/2003 | Dixon et al. | |
| 6,652,526 B1 * | 11/2003 | Arafiles | A61B 17/7032 606/264 |
| 6,682,533 B1 * | 1/2004 | Dinsdale | A61B 17/82 24/134 P |
| 6,706,044 B2 | 3/2004 | Kuslich et al. | |
| 6,749,612 B1 * | 6/2004 | Conchy | A61B 17/7044 606/250 |
| 6,835,196 B2 * | 12/2004 | Biedermann | A61B 17/7032 606/308 |
| 7,018,378 B2 * | 3/2006 | Biedermann | A61B 17/7037 606/265 |
| 7,166,109 B2 | 1/2007 | Biedermann et al. | |
| 7,344,537 B1 * | 3/2008 | Mueller | A61B 17/7037 606/278 |
| 7,491,221 B2 * | 2/2009 | David | A61B 17/7007 606/266 |
| 7,572,280 B2 * | 8/2009 | Dickinson | A61B 17/7007 606/266 |
| 7,588,588 B2 | 9/2009 | Spitler et al. | |
| 7,648,520 B2 * | 1/2010 | Markworth | A61B 17/7005 606/246 |
| 7,686,835 B2 * | 3/2010 | Warnick | A61B 17/7032 606/264 |
| 7,695,500 B2 * | 4/2010 | Markworth | A61B 17/7055 606/246 |
| 7,699,874 B2 * | 4/2010 | Young | A61B 17/705 606/250 |
| 7,717,941 B2 | 5/2010 | Petit | |
| 7,789,895 B2 * | 9/2010 | Heinz | A61B 17/7055 606/246 |
| 7,803,174 B2 * | 9/2010 | Denis | A61B 17/7035 606/250 |
| 7,806,912 B2 * | 10/2010 | Lawton | A61B 17/7049 606/250 |
| 7,892,259 B2 * | 2/2011 | Biedermann | A61B 17/7032 606/246 |

(56) References Cited

U.S. PATENT DOCUMENTS

| | | | | |
|---|---|---|---|---|
| 7,896,905 B2* | 3/2011 | Lee | A61B 17/7037 | 606/268 |
| 7,909,854 B2* | 3/2011 | Schwab | A61B 17/705 | 606/250 |
| 7,942,907 B2* | 5/2011 | Richelsoph | A61B 17/7014 | 606/257 |
| 8,097,026 B2* | 1/2012 | Gorek | A61B 17/02 | 606/279 |
| 2001/0037111 A1* | 11/2001 | Dixon | A61B 17/66 | 606/261 |
| 2002/0055740 A1* | 5/2002 | Lieberman | A61B 17/70 | 606/263 |
| 2002/0068940 A1* | 6/2002 | Gaines, Jr. | A61B 17/7044 | 606/75 |
| 2002/0116001 A1* | 8/2002 | Schafer | A61B 17/7032 | 606/270 |
| 2002/0138077 A1* | 9/2002 | Ferree | A61B 17/7005 | 606/258 |
| 2002/0169448 A1* | 11/2002 | Vanacker | A61B 17/7049 | 606/250 |
| 2002/0169450 A1* | 11/2002 | Lange | A61B 17/7037 | 606/250 |
| 2003/0023243 A1* | 1/2003 | Biedermann | A61B 17/7032 | 606/308 |
| 2003/0032959 A1* | 2/2003 | Yeh | A61B 17/7001 | 606/261 |
| 2003/0045875 A1* | 3/2003 | Bertranou | A61B 17/701 | 606/261 |
| 2003/0144664 A1 | 7/2003 | Cavagna et al. | | |
| 2003/0144665 A1* | 7/2003 | Munting | A61B 17/7043 | 606/278 |
| 2003/0171755 A1* | 9/2003 | Moseley | A61B 17/7032 | 606/270 |
| 2003/0187435 A1* | 10/2003 | Lin | A61B 17/7001 | 606/250 |
| 2004/0015166 A1* | 1/2004 | Gorek | A61B 17/7049 | 606/251 |
| 2004/0039388 A1* | 2/2004 | Biedermann | A61B 17/6433 | 606/71 |
| 2004/0049197 A1* | 3/2004 | Barbera Alacreu | A61B 17/686 | 606/265 |
| 2004/0087949 A1* | 5/2004 | Bono | A61B 17/7035 | 606/278 |
| 2004/0092930 A1* | 5/2004 | Petit | A61B 17/7041 | 606/264 |
| 2004/0111088 A1* | 6/2004 | Picetti | A61B 17/7001 | 606/265 |
| 2004/0147929 A1* | 7/2004 | Biedermann | A61B 17/7001 | 606/266 |
| 2004/0153070 A1* | 8/2004 | Barker | A61B 17/7055 | 606/281 |
| 2004/0162558 A1* | 8/2004 | Hegde | A61B 17/7044 | 606/287 |
| 2004/0181224 A1* | 9/2004 | Biedermann | A61B 17/7032 | 606/266 |
| 2004/0186478 A1* | 9/2004 | Jackson | A61B 17/7032 | 606/300 |
| 2004/0199252 A1* | 10/2004 | Sears | A61B 17/025 | 623/17.11 |
| 2004/0215191 A1* | 10/2004 | Kitchen | A61B 17/7002 | 606/254 |
| 2004/0225289 A1* | 11/2004 | Biedermann | A61B 17/8605 | 606/257 |
| 2004/0249378 A1* | 12/2004 | Saint Martin | A61B 17/7032 | 606/86 A |
| 2004/0254577 A1* | 12/2004 | Delecrin | A61B 17/7007 | 606/261 |
| 2005/0004573 A1* | 1/2005 | Abdou | A61B 17/7059 | 606/246 |
| 2005/0010215 A1* | 1/2005 | Delecrin | A61B 17/7007 | 606/261 |
| 2005/0055026 A1* | 3/2005 | Biedermann | A61B 17/1659 | 606/278 |
| 2005/0085815 A1 | 4/2005 | Harms et al. | | |
| 2005/0113831 A1* | 5/2005 | Franck | A61B 17/7052 | 606/250 |
| 2005/0131404 A1* | 6/2005 | Mazda | A61B 17/7041 | 606/264 |
| 2005/0149019 A1* | 7/2005 | Sasing | A61B 17/7049 | 606/250 |
| 2005/0154388 A1* | 7/2005 | Roussouly | A61B 17/7044 | 606/276 |
| 2005/0154390 A1* | 7/2005 | Biedermann | A61B 17/7035 | 128/898 |
| 2005/0171537 A1* | 8/2005 | Mazel | A61B 17/7037 | 606/264 |
| 2005/0197700 A1* | 9/2005 | Boehm, Jr. | A61F 2/4405 | 623/17.11 |
| 2005/0228378 A1* | 10/2005 | Kalfas | A61B 17/705 | 606/252 |
| 2005/0228381 A1* | 10/2005 | Kirschman | A61B 17/7031 | 623/17.15 |
| 2005/0240181 A1* | 10/2005 | Boomer | A61B 17/7041 | 606/914 |
| 2005/0240265 A1* | 10/2005 | Kuiper | A61B 17/7064 | 623/17.11 |
| 2005/0277920 A1* | 12/2005 | Slivka | A61B 17/7044 | 606/263 |
| 2005/0277923 A1* | 12/2005 | Sweeney | A61B 17/1671 | 623/17.11 |
| 2005/0277931 A1* | 12/2005 | Sweeney | A61B 17/1671 | 606/264 |
| 2005/0277932 A1* | 12/2005 | Farris | A61B 17/7014 | 606/260 |
| 2005/0288668 A1* | 12/2005 | Brinkhaus | A61B 17/701 | 606/254 |
| 2005/0288669 A1* | 12/2005 | Abdou | A61B 17/6433 | 606/246 |
| 2006/0064090 A1* | 3/2006 | Park | A61B 17/7005 | 606/250 |
| 2006/0064091 A1* | 3/2006 | Ludwig | A61B 17/7007 | 606/250 |
| 2006/0084993 A1* | 4/2006 | Landry | A61B 17/1604 | 606/86 A |
| 2006/0089644 A1* | 4/2006 | Felix | A61B 17/7037 | 606/250 |
| 2006/0095037 A1* | 5/2006 | Jones | A61B 17/7041 | 606/278 |
| 2006/0142758 A1 | 6/2006 | Petit | | |
| 2006/0173456 A1* | 8/2006 | Hawkes | A61B 17/7037 | 606/278 |
| 2006/0206114 A1* | 9/2006 | Ensign | A61B 17/7034 | 606/278 |
| 2006/0247629 A1* | 11/2006 | Maughan | A61B 17/6466 | 606/53 |
| 2006/0276789 A1* | 12/2006 | Jackson | A61B 17/7032 | 606/916 |
| 2007/0049937 A1 | 3/2007 | Matthis et al. | | |
| 2007/0173828 A1* | 7/2007 | Firkins | A61B 17/7043 | 606/261 |
| 2007/0225708 A1* | 9/2007 | Biedermann | A61B 17/7022 | 606/279 |
| 2007/0233073 A1 | 10/2007 | Wisnewski et al. | | |
| 2007/0288008 A1 | 12/2007 | Park | | |
| 2008/0058818 A1* | 3/2008 | Schwab | A61B 17/7032 | 606/328 |
| 2008/0065074 A1* | 3/2008 | Yeung | A61B 17/7032 | 606/269 |
| 2008/0071277 A1* | 3/2008 | Warnick | A61B 17/7037 | 606/258 |
| 2008/0103501 A1* | 5/2008 | Ralph | A61F 2/4405 | 606/254 |
| 2008/0103502 A1* | 5/2008 | Capote | A61B 17/7007 | 606/257 |
| 2008/0114362 A1* | 5/2008 | Justis | A61B 17/7002 | 606/267 |

(56) References Cited

U.S. PATENT DOCUMENTS

| | | | |
|---|---|---|---|
| 2008/0161854 A1* | 7/2008 | Bae | A61B 17/7007 606/246 |
| 2008/0161858 A1* | 7/2008 | Mahoney | A61B 17/7044 606/265 |
| 2008/0177323 A1* | 7/2008 | Null | A61B 17/705 606/267 |
| 2008/0177326 A1* | 7/2008 | Thompson | A61B 17/7047 606/277 |
| 2008/0177328 A1* | 7/2008 | Perez-Cruet | A61B 17/7005 606/279 |
| 2008/0177335 A1* | 7/2008 | Melkent | A61B 17/7001 606/309 |
| 2008/0234736 A1* | 9/2008 | Trieu | A61B 17/7026 606/250 |
| 2008/0234757 A1* | 9/2008 | Jacofsky | A61B 17/7032 606/308 |
| 2008/0243185 A1* | 10/2008 | Felix | A61B 17/7032 606/246 |
| 2008/0243186 A1* | 10/2008 | Abdou | A61B 17/7067 606/246 |
| 2008/0249570 A1* | 10/2008 | Carson | A61B 17/7038 606/264 |
| 2008/0255556 A1* | 10/2008 | Berger | A61B 17/8605 606/60 |
| 2008/0255617 A1* | 10/2008 | Cho | A61B 17/702 606/246 |
| 2008/0262545 A1* | 10/2008 | Simonson | A61B 17/7007 606/247 |
| 2008/0262546 A1* | 10/2008 | Calvosa | A61B 17/701 606/250 |
| 2008/0262550 A1* | 10/2008 | Ferree | A61B 17/70 606/263 |
| 2008/0262551 A1* | 10/2008 | Rice | A61B 17/8869 606/268 |
| 2008/0262552 A1* | 10/2008 | Kim | A61B 17/7011 606/276 |
| 2008/0262553 A1* | 10/2008 | Hawkins | A61B 17/705 606/278 |
| 2008/0269810 A1* | 10/2008 | Zhang | A61B 17/7001 606/305 |
| 2008/0275456 A1* | 11/2008 | Vonwiller | A61B 17/7032 606/246 |
| 2008/0306549 A1* | 12/2008 | Winslow | A61B 17/7035 606/264 |
| 2009/0005813 A1* | 1/2009 | Crall | A61B 17/7035 606/246 |
| 2009/0005817 A1* | 1/2009 | Friedrich | A61B 17/7007 606/246 |
| 2009/0062864 A1* | 3/2009 | Ludwig | A61B 17/705 606/301 |
| 2009/0076552 A1* | 3/2009 | Tornier | A61B 17/7038 606/264 |
| 2009/0099604 A1* | 4/2009 | Cho | A61B 17/7049 606/250 |
| 2009/0105755 A1* | 4/2009 | Capote | A61B 17/7007 606/246 |
| 2009/0131982 A1* | 5/2009 | Schwab | A61B 17/7001 606/246 |
| 2009/0204156 A1* | 8/2009 | McClintock | A61B 17/7002 606/278 |
| 2009/0216282 A1* | 8/2009 | Blake | A61B 17/7059 606/286 |
| 2009/0259254 A1* | 10/2009 | Pisharodi | A61B 17/7034 606/246 |
| 2009/0281571 A1* | 11/2009 | Weaver | A61B 17/025 606/246 |
| 2009/0299412 A1* | 12/2009 | Marino | A61B 17/1637 606/246 |
| 2009/0299413 A1* | 12/2009 | Miller | A61B 17/7052 606/278 |
| 2009/0318973 A1* | 12/2009 | Moulin | A61B 17/6466 606/278 |
| 2009/0318974 A1* | 12/2009 | Yuan | A61B 17/7032 606/279 |
| 2010/0004689 A1* | 1/2010 | Biyani | A61B 17/7004 606/250 |
| 2010/0023058 A1* | 1/2010 | Tornier | A61B 17/7049 606/246 |
| 2010/0036420 A1* | 2/2010 | Kalfas | A61B 17/7007 606/250 |
| 2010/0069961 A1* | 3/2010 | DiPoto | A61B 17/7011 606/249 |
| 2010/0087863 A1* | 4/2010 | Biedermann | A61B 17/7029 606/261 |
| 2010/0087865 A1* | 4/2010 | Biedermann | A61B 17/7037 606/264 |
| 2010/0094348 A1* | 4/2010 | Biedermann | A61B 17/7037 606/264 |
| 2010/0094349 A1* | 4/2010 | Hammer | A61B 17/7034 606/264 |
| 2010/0114167 A1* | 5/2010 | Wilcox | A61B 17/7004 606/250 |
| 2010/0137911 A1* | 6/2010 | Dant | A61B 17/7004 606/252 |
| 2010/0152778 A1* | 6/2010 | Saint Martin | A61B 17/7037 606/279 |
| 2010/0160981 A1* | 6/2010 | Butler | A61B 17/7037 606/308 |
| 2010/0174315 A1* | 7/2010 | Scodary | A61B 17/7052 606/248 |
| 2010/0191293 A1* | 7/2010 | Jackson | A61B 17/8605 606/302 |
| 2010/0198262 A1* | 8/2010 | McKinley | A61B 17/7041 606/265 |
| 2010/0211104 A1* | 8/2010 | Moumene | A61B 17/7028 606/257 |
| 2010/0222750 A1* | 9/2010 | Cheng | A61F 2/442 604/288.04 |
| 2010/0234902 A1* | 9/2010 | Biedermann | A61B 17/7032 606/305 |
| 2010/0262189 A1* | 10/2010 | Park | A61B 17/7011 606/254 |
| 2010/0268279 A1* | 10/2010 | Gabelberger | A61B 17/7035 606/278 |
| 2010/0298884 A1* | 11/2010 | Faizan | A61B 17/7052 606/266 |
| 2010/0305621 A1* | 12/2010 | Wang | A61B 17/8605 606/305 |
| 2010/0312279 A1* | 12/2010 | Gephart | A61B 17/3421 606/264 |
| 2010/0312287 A1* | 12/2010 | Jackson | A61B 17/7028 606/302 |
| 2010/0318131 A1* | 12/2010 | James | A61B 17/7005 606/264 |
| 2010/0318136 A1* | 12/2010 | Jackson | A61B 17/7037 606/305 |
| 2010/0324599 A1* | 12/2010 | Montello | A61B 17/7001 606/264 |
| 2010/0331890 A1* | 12/2010 | Drewry | A61B 17/7031 606/279 |
| 2011/0004256 A1* | 1/2011 | Biedermann | A61B 17/7098 606/301 |
| 2011/0015683 A1* | 1/2011 | Jackson | A61B 17/7037 606/305 |
| 2011/0040331 A1* | 2/2011 | Fernandez | A61B 17/701 606/264 |
| 2011/0046683 A1* | 2/2011 | Biedermann | A61B 17/7035 606/305 |
| 2011/0060365 A1* | 3/2011 | Felix | A61B 17/7002 606/246 |
| 2011/0060367 A1* | 3/2011 | Stauber | A61B 17/7049 606/250 |
| 2011/0071577 A1* | 3/2011 | Barker, Jr. | A61B 17/7037 606/302 |
| 2011/0077692 A1* | 3/2011 | Jackson | A61B 17/861 606/304 |
| 2011/0087291 A1* | 4/2011 | Justis | A61B 17/7004 606/264 |

(56) References Cited

U.S. PATENT DOCUMENTS

| | | | |
|---|---|---|---|
| 2011/0098755 A1* | 4/2011 | Jackson | A61B 17/7008 606/305 |
| 2011/0106165 A1* | 5/2011 | Schwab | A61B 17/7022 606/264 |
| 2011/0106168 A1* | 5/2011 | Bucci | A61B 17/7071 606/264 |
| 2011/0152941 A1* | 6/2011 | Graf | A61B 17/7007 606/277 |
| 2011/0160778 A1* | 6/2011 | Elsbury | A61B 17/7037 606/305 |
| 2011/0178558 A1* | 7/2011 | Barry | A61B 17/8605 606/302 |
| 2011/0178559 A1* | 7/2011 | Barry | A61B 17/7032 606/302 |
| 2011/0184463 A1* | 7/2011 | Schwend | A61B 17/705 606/258 |
| 2011/0218578 A1* | 9/2011 | Jackson | A61B 17/86 606/305 |
| 2011/0218579 A1* | 9/2011 | Jackson | A61B 17/7032 606/305 |
| 2011/0245880 A1* | 10/2011 | Lawrence | A61B 17/7001 606/279 |
| 2011/0245883 A1* | 10/2011 | Dall | A61B 17/7035 606/305 |
| 2011/0257690 A1* | 10/2011 | Rezach | A61B 17/7037 606/302 |
| 2011/0263945 A1* | 10/2011 | Peterson | A61B 17/7074 600/213 |
| 2011/0264151 A1* | 10/2011 | Davis | A61B 17/7035 606/305 |
| 2011/0270314 A1* | 11/2011 | Mueller | A61B 17/704 606/264 |
| 2012/0029568 A1* | 2/2012 | Jackson | A61B 17/702 606/264 |
| 2012/0116462 A1* | 5/2012 | Arambula | A61B 17/7037 606/305 |
| 2012/0116463 A1* | 5/2012 | Razian | A61B 17/7032 606/305 |
| 2012/0123486 A1* | 5/2012 | Werner | A61B 17/7037 606/308 |
| 2012/0310284 A1* | 12/2012 | Gerchow | A61B 17/7037 606/264 |
| 2012/0310290 A1* | 12/2012 | Jackson | A61B 17/7037 606/304 |
| 2013/0053901 A1* | 2/2013 | Cormier | A61B 17/7037 606/305 |
| 2013/0060293 A1* | 3/2013 | Jackson | A61B 17/7037 606/305 |
| 2013/0066380 A1* | 3/2013 | Haskins | A61B 17/7035 606/305 |

FOREIGN PATENT DOCUMENTS

| | | |
|---|---|---|
| EP | 1 795 134 A1 | 6/2007 |
| EP | 1 810 624 A1 | 7/2007 |
| EP | 1 891 904 A1 | 2/2008 |
| EP | 1 923 011 A1 | 5/2008 |
| WO | WO 03/034930 A1 | 5/2003 |
| WO | WO 2004/105577 A2 | 12/2004 |
| WO | WO 2006/066685 A1 | 6/2006 |
| WO | WO 2007/038429 A1 | 4/2007 |
| WO | WO 2007/060534 A2 | 5/2007 |

* cited by examiner

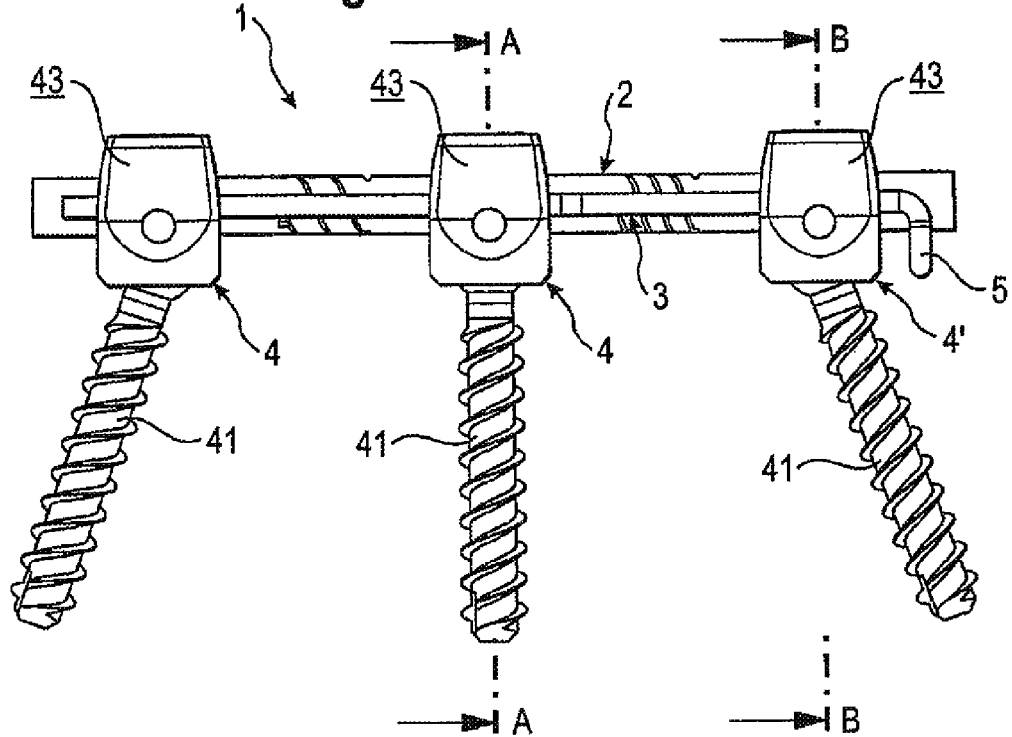
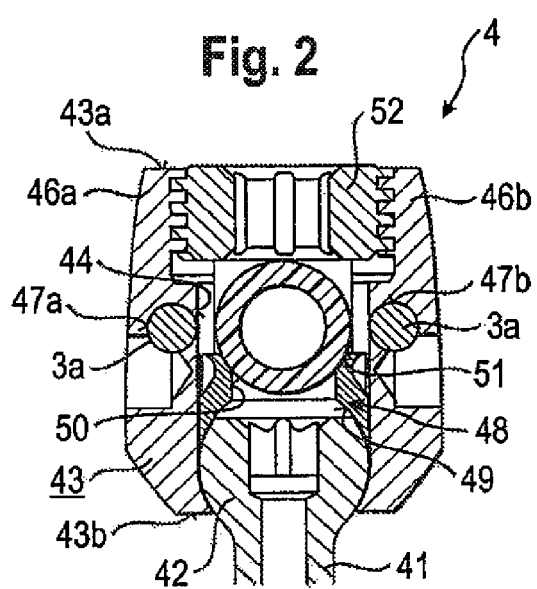
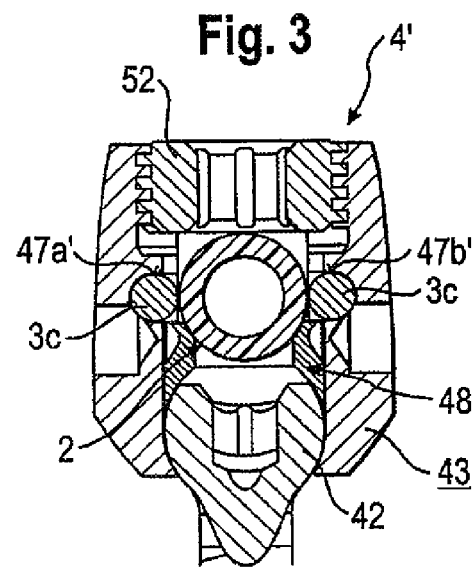

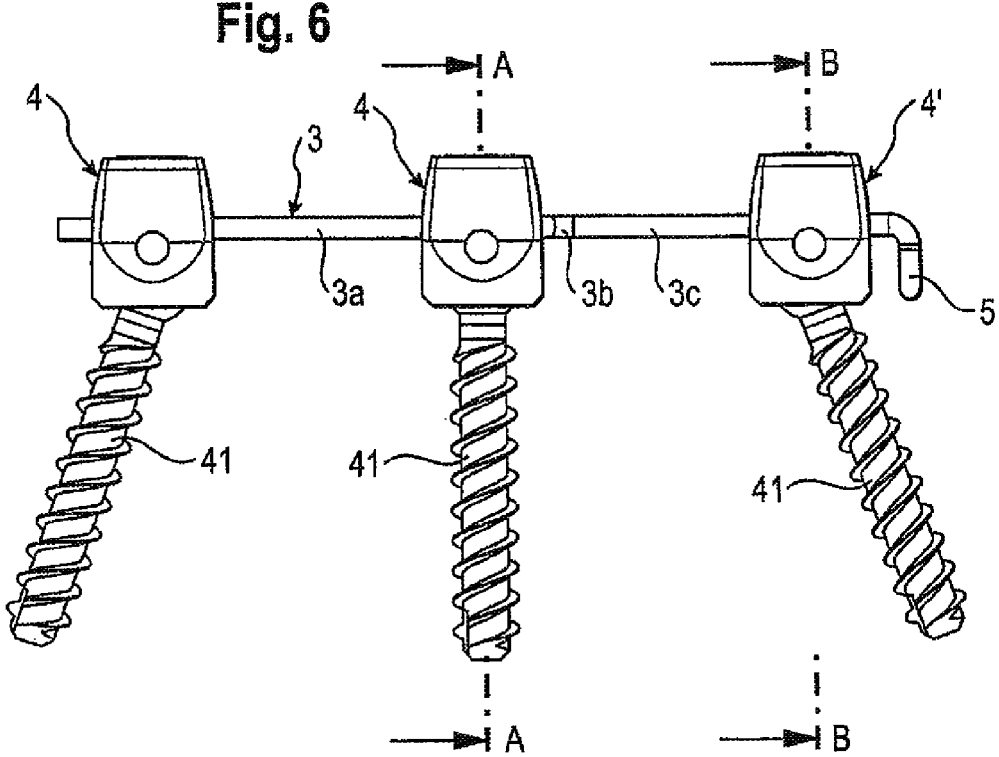
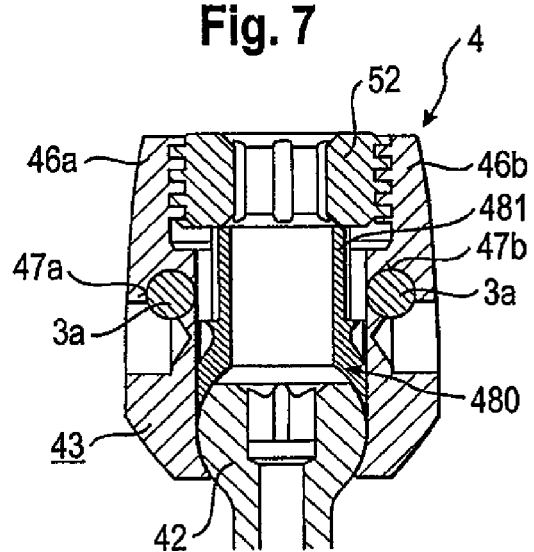
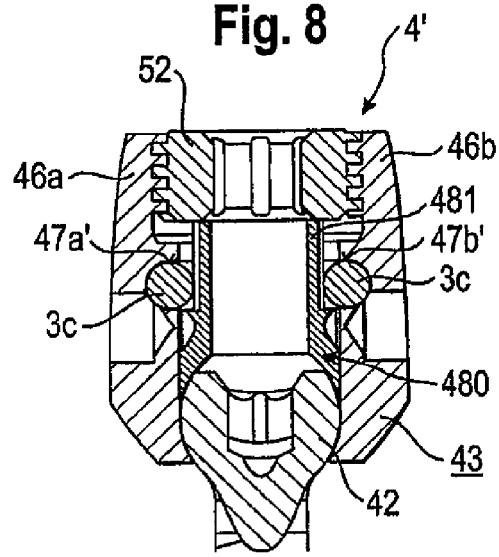

BONE ANCHORING ELEMENT AND STABILIZATION DEVICE FOR BONES, IN PARTICULAR FOR THE SPINAL COLUMN

CROSS-REFERENCE TO RELATED APPLICATION(S)

This application is a continuation of U.S. patent application Ser. No. 12/550,654, filed Aug. 31, 2009, which claims the benefit of U.S. Provisional Patent Application Ser. No. 61/094,664, filed Sep. 5, 2008, the contents of which are hereby incorporated by reference in their entirety, and claims priority from European Patent Application EP 08 015 721.7, filed Sep. 5, 2008, the contents of which are hereby incorporated by reference in their entirety.

BACKGROUND

The present application relates to a bone anchoring element and to a stabilization device for bones, in particular for the spinal column, including such a bone anchoring element.

In the case of replacement of a severely injured or degenerated intervertebral disc or vertebra by fusion cages or bone segments stabilization devices using rigid metal rods are commonly used which are anchored in the neighboring vertebrae by polyaxial bone screws.

In specific clinical applications it is advantageous to maintain a certain mobility of the motion segments of the spinal column. In these cases, a dynamic stabilization system having bone anchoring elements and flexible rods are used. For example, US 2005/0085815 A1 and US 2007/0049937 A1 describe dynamic stabilization systems having a hollow metallic rod with a flexible section formed by a helix-shaped recess in the wall and a core provided in the hollow rod.

A dynamic stabilization device using polyaxial screws and an elastomer rod is described in EP 1 795 134 A1.

The known stabilization devices with flexible rods are suitable for the dynamic stabilization and motion control of the spinal column with respect to axial tension and compression forces.

Due to the anatomy of the spinal column, small sized implant constructs are required. Therefore, the flexible rods should have small outer diameters which makes it possible to design the receiving part of the polyaxial screw with a low profile and small overall dimensions.

In clinical cases of early degeneration or partial damages or injuries of intervertebral discs, the corresponding motion segments of the spinal column are subject to increased rotational movements and/or increased shearing forces. Such rotational movements and shearing and/or bending forces can cause strong pain. In addition, the flexible rods made of metal or elastomers may not be able to withstand higher forces for a long time due to their small diameter. In particular, shearing and rotational forces may cause an overload of the flexible rod.

Based on the foregoing, there is a need to provide a bone anchoring element and a stabilization device, in particular for the spinal column, which is suitable for cases in which increased rotational and shearing movements of the spinal column are present.

SUMMARY

A disclosed bone anchoring element includes a receiving part having a U-shaped recess forming a channel in which a stabilizing rod can be inserted and additionally includes lateral guides for accommodating connection rods with a smaller diameter. A disclosed stabilization device includes at least two such bone anchoring elements and at least one connection rod. The bone anchoring element is preferably a polyaxial bone screw.

The bone anchoring element and the stabilization device has an increased resistance against shearing and rotational forces without hindering the axial damping and the precision adjustment of the stabilization device and it offers a modular system allowing various combinations of flexible rods and connection rods.

BRIEF DESCRIPTION OF THE DRAWINGS

FIG. 1 shows a side view of the stabilization device according to a first embodiment.

FIG. 2 shows an enlarged sectional view along line A-A in FIG. 1.

FIG. 3 shows an enlarged sectional view along line B-B in FIG. 1.

FIG. 6 shows a side view of the stabilization device according to a second embodiment.

FIG. 7 shows an enlarged sectional view along line A-A of FIG. 6.

FIG. 8 shows an enlarged sectional view along line B-B of FIG. 6.

DETAILED DESCRIPTION

Figure 4:
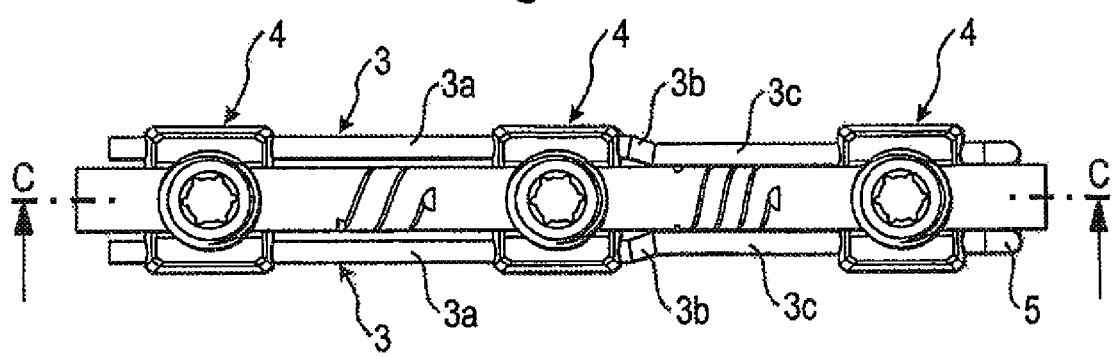
FIG. 4 shows a top view of the stabilization device of FIG. 1.

As shown in FIGS. 1 to 5 the bone stabilization device 1 according to a first embodiment includes a flexible rod 2 and at least one laterally arranged connection rod 3 which are both connected to bone anchoring elements 4, 4'.

The flexible rod 2 includes at least a portion 2a exhibiting flexibility under the action of compression and extension forces acting along the rod axis and under the action of torsional, shearing and/or bending forces. In the embodiment shown, the flexible rod 2 is made of a hollow tube of a rigid material, such as a body compatible metal, metal alloy, in particular of titanium, Nitinol, stainless steel or of a rigid body compatible plastic material such as PEEK or carbon fiber reinforced PEEK. The length of the flexible rod is such that it spans at least the distance between two adjacent vertebrae. In the embodiment shown, the flexible rod spans the distance between three adjacent vertebrae. The flexible portion 2a is provided between rigid portions 2b. The rigid portions 2b are connected to the bone anchoring elements. The flexibility of the flexible portion is achieved by a helix-shaped recess in the wall of the hollow tube. However, any other design conferring flexibility to the rod is possible.

At both sides of the flexible rod 2 a solid connection rod 3 is arranged the diameter of which is smaller than that of the flexible rod 2. The length of each of the connection rods 3 can be the same as that of the flexible rod 2 or can be smaller than that of the flexible rod 2. In the embodiment shown, the connection rods 3 are not fully straight, but have a first straight section 3a, a step portion 3b and a second straight section 3c. The connection rods 3 are preferably less flexible when compared to the flexible section 2a of the flexible rod 2. For example, the connection rods 3 are made of a body compatible metal such as stainless steel, titanium, titanium alloys such as Nitinol or a rigid plastic material such as PEEK or carbon reinforced PEEK.

The diameter of the connections rods 3 is considerably smaller than that of the flexible stabilization rod 2. However, the diameter of the connections rods 3 has to have such a size that the connection rods 3 are rigid enough to resist bending forces.

The two lateral connection rods 3 are connected to each other at one of their respective ends by means of a bracket 5 which is formed such that it is orientated downwards or upwards in order to circumvent the flexible rod 2. The bracket 5 can be integrally formed with the rods 3 or can be a separate part which is connectable to the rods 3.

The bone anchoring element 4 is designed in the form of a polyaxial bone screw. It includes a screw element having a threaded shank 41 and spherically shaped head 42 and a receiving part 43 for receiving the flexible rod 2 and the connection rods 3. The receiving part 3 has a substantially cylindrical or cuboid shape with a first end 43a and an opposite second end 43b and a coaxial bore 44 extending from the first end 43a in the direction of the second end 43b and tapering towards the second end such that a seat is provided for the head 42 of the screw element which is pivotably held in the receiving part.

Figure 5:
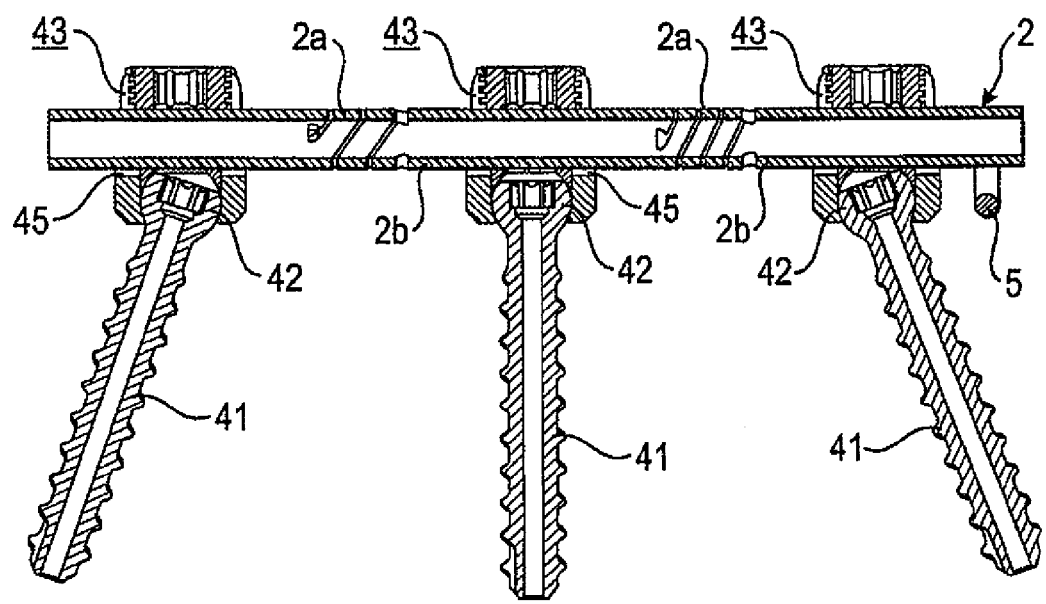
FIG. 5 shows a sectional view of the stabilization device of FIG. 4 along line C-C.
Figure 9:
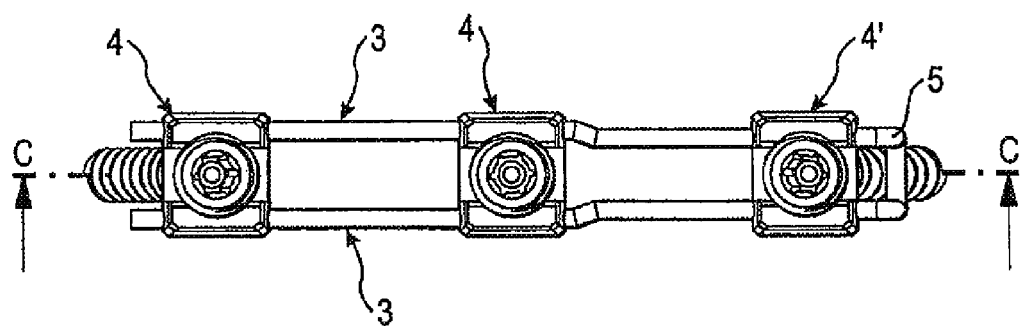
FIG. 9 shows a top view of the stabilization device of FIG. 6.
Figure 10:
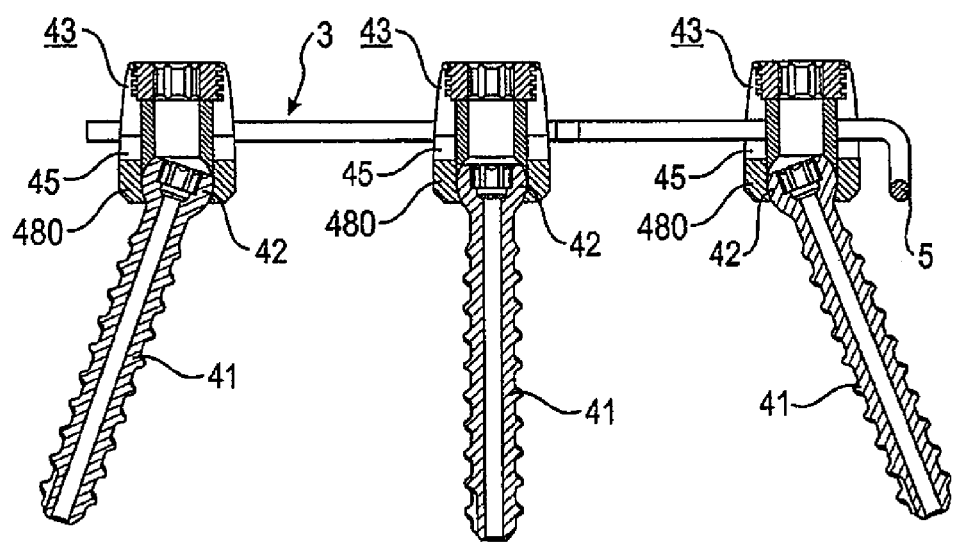
FIG. 10 shows a sectional view along C-C of FIG. 9.

As can be seen in particular in FIG. 5 the receiving part 43 includes a substantially U-shaped recess 45 extending from the first end 43a in the direction of the second end 43b. By means of the U-shaped recess two free legs 46a, 46b are formed which form together with the bottom of the recess a channel for accommodating the flexible rod 2.

In the wall of each of the free legs 46a, 46b bores 47a, 47b are provided and which form guides for the connection rods. The bores 47a, 47b extend through the free legs 46a, 46 so that the connection rods 3 can be guided through the bores from one side of the receiving part and exit through the other side. The size of the bores is such that the diameter is slightly larger than the outer diameter of the connection rods 3 to allow a sliding movement of the connection rods 3 within the bores 47a, 47b.

In the embodiment shown in FIG. 2 the bores 47a, 47b are located fully within the free legs 46a and 46b and form through holes. The location of the through holes 47a, 47b is such that the bore axis is in one plane with the axis of the flexible rod 2 when the flexible rod 2 is inserted.

The polyaxial bone screw further includes a pressure element 48 which is substantially cylindrical so as to be movable in the bore 44 and which has on its side facing the head 42 a spherical recess 49 to encompass a portion of the head to distribute the pressure onto the head 42. It further includes a coaxial bore 50 to allow access to the head 42. On its side opposite to the spherical recess the pressure element 48 has a cylinder segment-shaped recess 51 which is sized such that the flexible rod 2 can be inserted and guided therein. In the embodiment shown in FIGS. 2 and 3 the cylinder segment-shaped recess 51 is sized such that the flexible rod projects above the pressure element.

The bone anchoring element further includes a fixation screw 52 which engages with an inner thread of the free legs 46a, 46b. The fixation screw 52 serves for pressing onto the flexible rod 2 in the receiving part and therefore indirectly pressing onto the pressure element 48 for exerting pressure onto the head 42 to lock the angular position of the screw element with respect to the receiving part.

FIG. 3 shows a bone anchoring element 4' which is a modification of the bone anchoring element which is suitable for accommodating the portion 3c of the connection rods shown in FIG. 4. It differs from the bone anchoring element according to FIG. 2 in the construction of the bores 47a', 47b'. All other elements of the bone anchoring element are the same as those of the bone anchoring element of FIG. 2 and the description thereof will not be repeated. The bores 47a', 47b' have a semi-circular cross section. The bores are open to the channel which accommodates the flexible rod 2. The connection rods 3 are secured from inside the receiving part by the flexible rod 2 against falling out from the bores 47a', 47b'. With this embodiment, it is possible to arrange the connection rods 3 more closely to the flexible rod 2 and the connection rods can be put in place through the U-shaped channel. As particularly shown in FIGS. 1 and 4, with this construction it is possible to span several motion segments of the spinal column with different distances of the flexible rod 2 and the connection rods 3 from each other.

Although the first embodiment shows that the connection rods 3 can be connected with each other with a integrally formed bracket 5, other possibilities are possible. For example, the connection rods can be mechanically connected at one or at both ends with a connection which is applied after the rods have been introduced into the receiving parts. They must not necessarily be connected, but can be single rods. To avoid that the single rods escape from the receiving parts in the course of their sliding movement, one end of the rods 3 can have a larger diameter which prevents sliding through the guides.

Although the connection rods are shown as cylindrical rods, the cross section of the connection rods may be non-circular, for example oval-shaped, polygon-shaped or otherwise shaped.

Although the outer shape along the rod axis is shown to have a bent portion 3b in FIG. 4, the connection rods can be straight.

With the bone anchoring element shown in FIG. 2, the connection rods are secured within the bores 47a, 47b against escaping. In specific clinical applications it may be possible to use a stabilizing device without the flexible rod.

The bracket 5 shown in FIG. 1 not only serves for connection of the connection rods 3 but also forms a stop for the sliding movement of the connection rods 3. It is also possible to provide a stop at the opposite end at a distance from the anchoring element 4 so that the connection rods 3 are still fully movable.

The guides and/or the connection rods can be provided with materials and/or devices for facilitating sliding of the connection rods 3. Such materials and/or devices can be, for example, coating, sliding guides or sliding bearings.

FIGS. 6 to 10 show a second embodiment of the stabilization device which differs from the first embodiment shown in FIGS. 1 to 5 only by the pressure element 480 compared to the pressure element 48. The pressure element 480 which allows to omit the flexible rod 2 and to provide stabilization only via the connection rods 3. All other elements and parts are identical to the first embodiment and the description thereof will not be repeated.

The pressure element 480 has instead of the cylinder segment-shaped recess 51 a cylindrical portion 481 which extends coaxially to the main portion of the pressure element and has a diameter which is smaller than the main portion. The length of the cylindrical portion 481 is such that the pressure element extends up to the fixation screw 52 so that the fixation screw 52 can press the pressure element 480 downwards when it is tightened. This embodiment is particularly suitable for applications where a flexible rod is not necessary. If the stabilization device is used without a flexible rod a shown in FIGS. 6 to 10, the pressure element 480 can be used instead of the pressure element 48 while all other parts of the first embodiment remaining the same. Hence, the construction of the bone anchoring element with respect to the bores 47a, 47b or 47a', 47b' remains the same.

Figure 11:
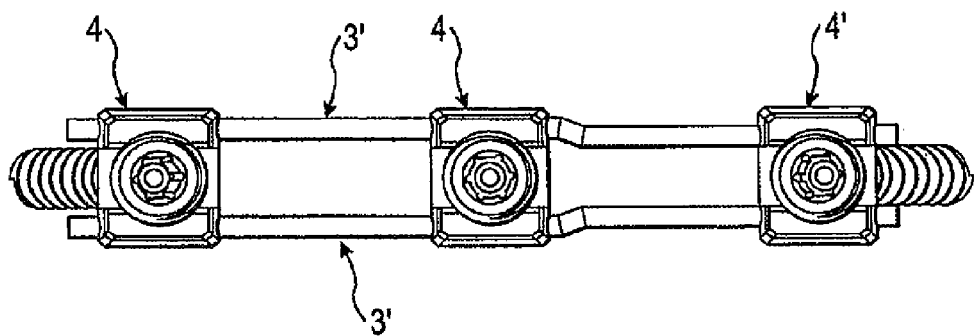
FIG. 11 shows a third embodiment of the stabilization device in a top view.
Figure 12:
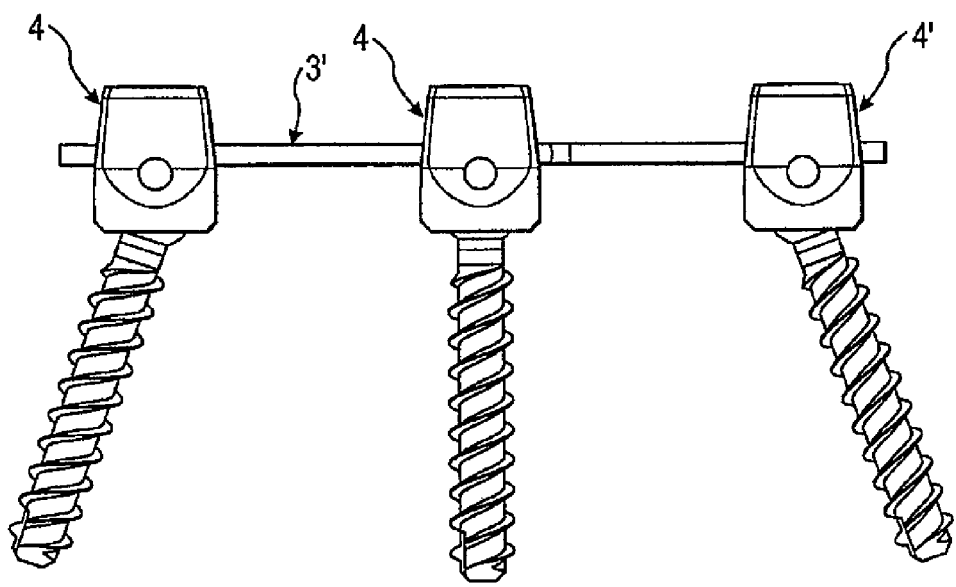
FIG. 12 shows a side view of the stabilization device of FIG. 11.
Figure 13:
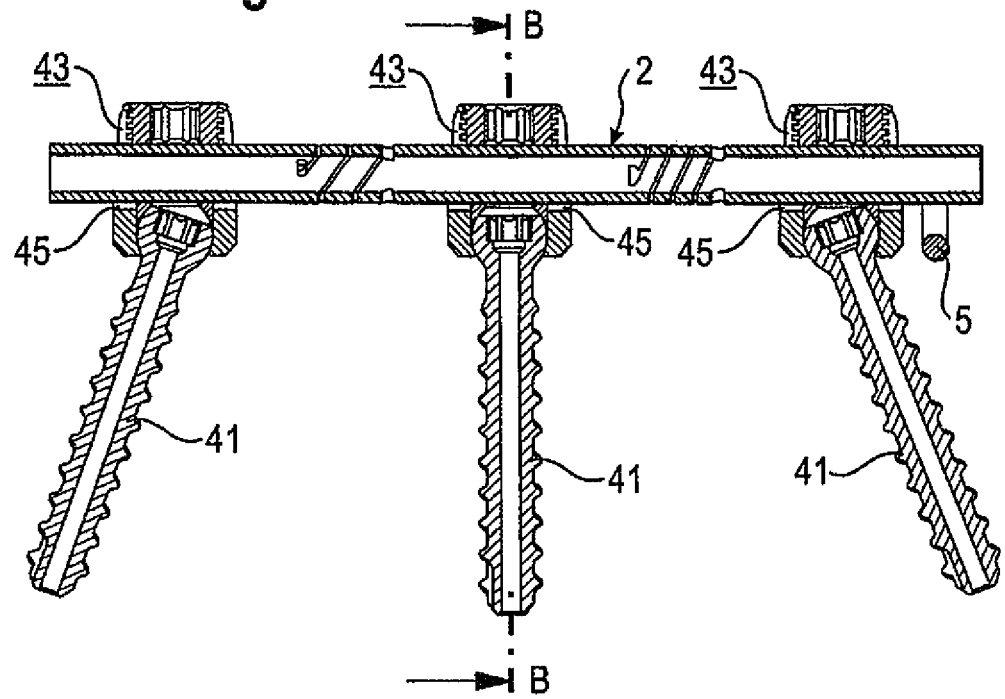
FIG. 13 shows a fourth embodiment of the stabilization device in a sectional view along the rod axis.
Figure 14:
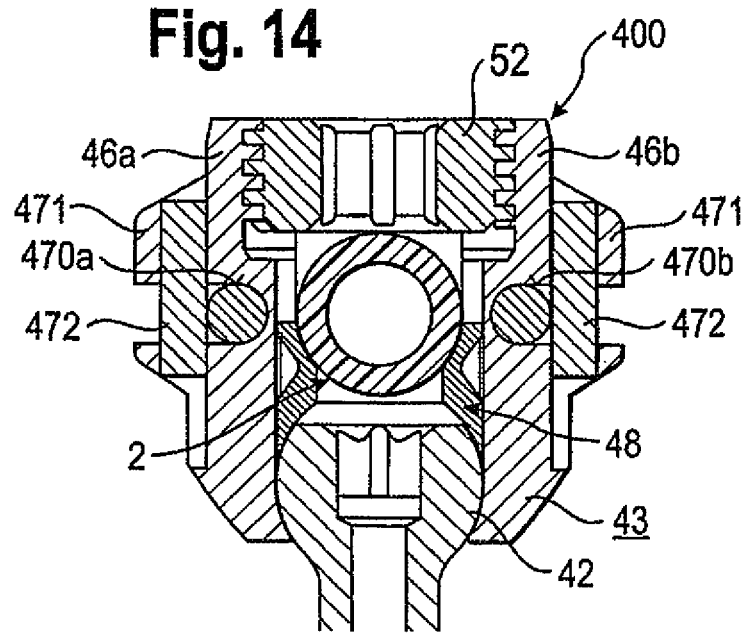
FIG. 14 shows an enlarged sectional view along line B-B of FIG. 13.
Figure 15:
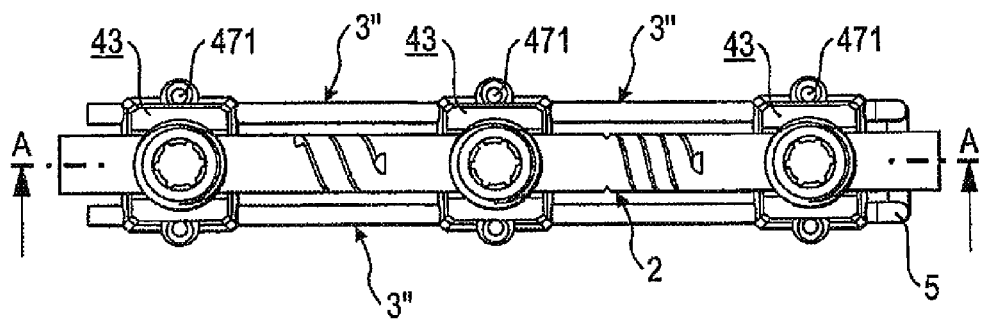
FIG. 15 shows a top view of the stabilization device of FIG. 13.
Figure 16:
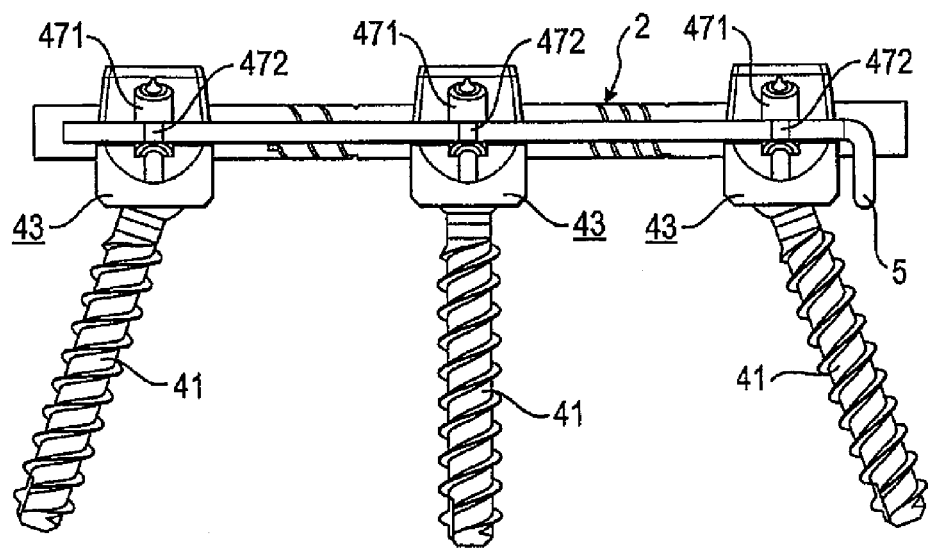
FIG. 16 shows a side view of the stabilization device of FIG. 15.
Figure 17:
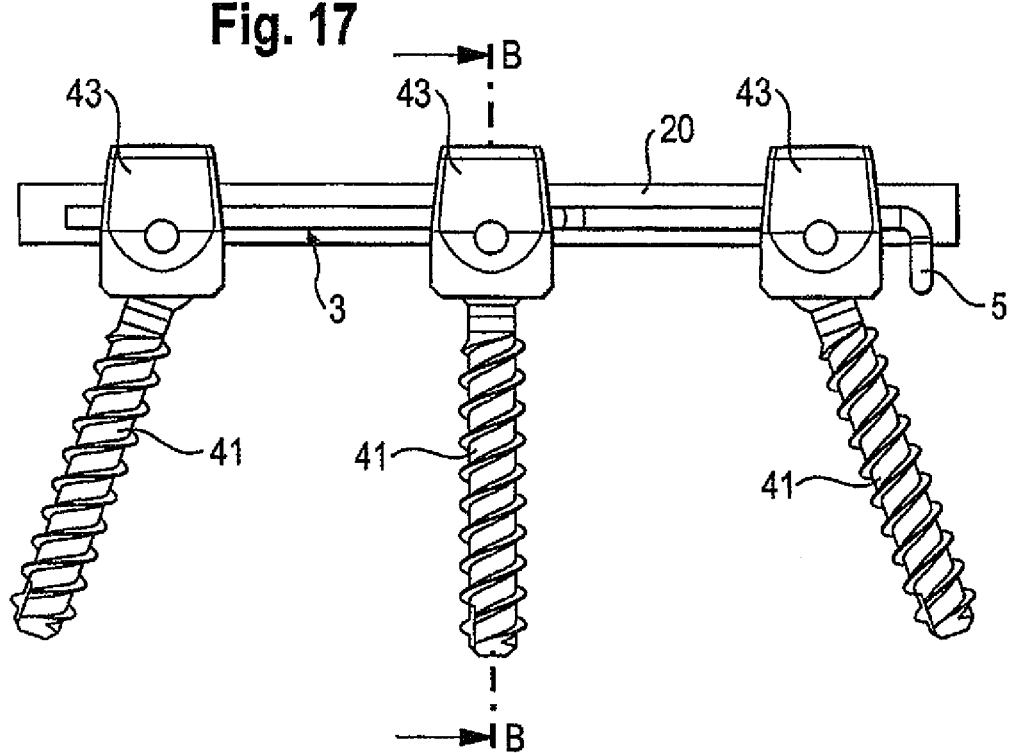
FIG. 17 shows a fifth embodiment of the stabilization device in a side view.

FIGS. 11 and 12 show a third embodiment of the stabilization device which differs from the second embodiment according to FIGS. 6 to 10 only in that the bracket 5 connecting the rods 3 is omitted. In such a case, it is advantageous to provide stops at both ends of the connection rods to allow a free but limited movement of the connecting rods in the receiving parts.

FIGS. 13 to 16 show a fourth embodiment of the stabilization device. In this embodiment a flexible rod 2 and fully straight connection rods 3 are used which are connected by the bracket 5. In this case, the assembly of the connection rods 3 can be introduced in the receiving parts simultaneously by gripping the bracket.

The bone anchoring element 400 of the fourth embodiment differs from the bone anchoring element 4 described in connection with the first embodiment by the location and design of the guides for guiding the connection rods 3. The free legs 46a, 46b have recesses 470a, 470b which are at the outer surface and are open to the outside of the receiving part. The cross section of the recesses 470a, 470b is substantially U-shaped and the size is such that the connection rods 3 can slide therein. To prevent escaping of the rods 3, the free legs 46a, 46b have a support structure 471 supporting a closure element 472, for example a closure bar, which closes the recess 470a, 470b respectively. The recesses 470a, 470b are located at the same height as the bores 47a, 47b of the first embodiment.

All other portions of the bone anchoring element 400 are identical to those of the first embodiment. It shall be noted that the bone anchoring element 400 can also be provided with a pressure element 480 described before when the use of a flexible rod 2 is not necessary.

Figure 18:
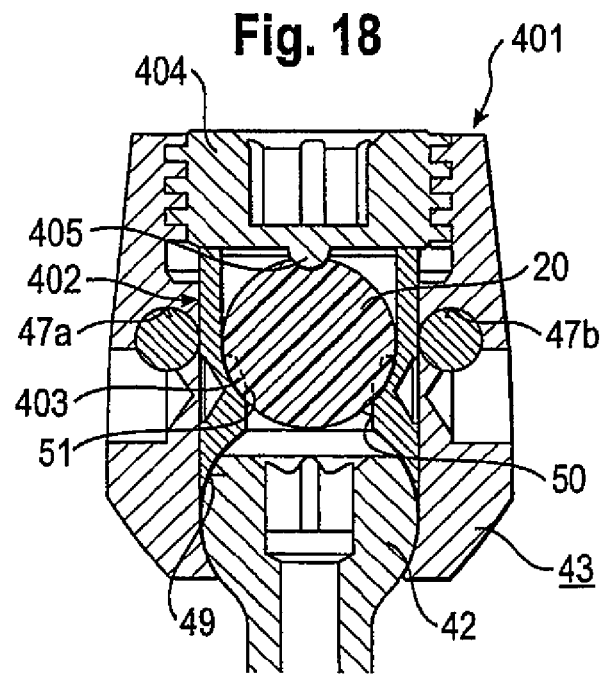
FIG. 18 shows an enlarged sectional view along line B-B of FIG. 17.
Figure 19:
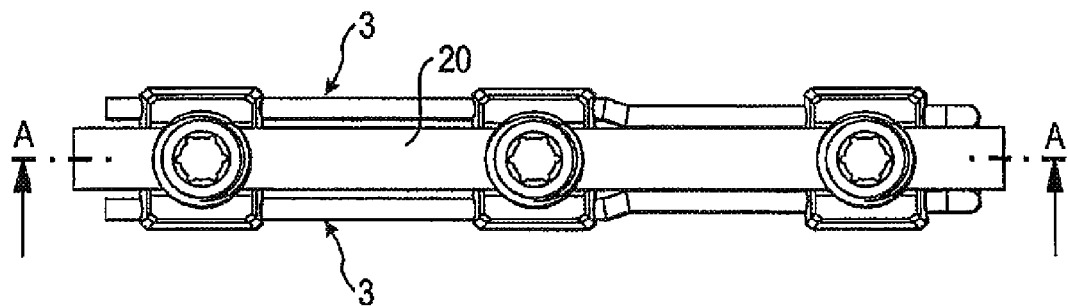
FIG. 19 shows a top view of the fifth embodiment of the stabilization device.
Figure 20:
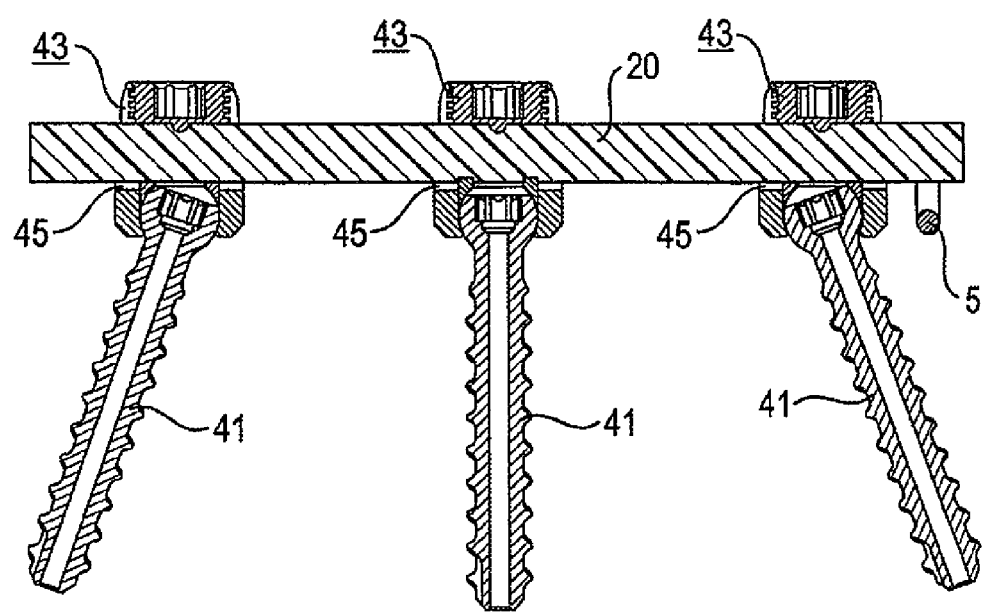
FIG. 20 shows a sectional view of the stabilization device of FIG. 19 along line A-A.

The stabilization device of a fifth embodiment according to FIGS. 17 to 20 has instead of the flexible rod 2 which is a hollow tube with a flexible section, a flexible rod 20 which is made of a flexible plastic material such as an elastomer, for example polyurethane, polycarbonateurethane (PCU) or polysiloxane. The flexible rod 20 exhibits axial flexibility under the action of axial extension or compression. The bone anchoring element 401 is adapted to clamp the flexible rod 20 as can be seen in FIG. 18. The bone anchoring element 401 includes bores 47a, 47b in the wall of the legs as described with respect to the first embodiment and differs from the bone anchoring element of the first embodiment by the shape of the pressure element 402 and the fixation element 404. The pressure element 402 extends above the surface of the flexible rod 20 when the flexible rod 20 is inserted. On the bottom of the recess 51 projections 403 are formed which engage in the surface of the flexible rod 20. The fixation element 404 is a fixation screw as in the first embodiment. However, it has a projection 405 on its lower side facing the flexible rod 20 which engages in the surface structure of the flexible rod 20. By means of this construction the flexible rod 20 is clamped between the pressure element and the fixation screw without blocking the head 42 in the receiving part. The head 42 is locked in its angular position by tightening the fixation screw 404 so that the pressure element presses onto the head.

Although various embodiments have been described in detail the invention is not limited thereto. Single elements of each embodiment can be combined with the other embodiment. In particular, the guides for the connection rods 3 can be varied between the embodiments described. Although specific designs of polyaxial bone screws are described, other designs can also be used, for example polyaxial screws with two part locking elements, polyaxial screws wherein the screw element is loaded into the receiving part from the top or from the bottom, polyaxial screws with various shapes of pressure elements to lock the angular position of the screw element with respect to the receiving part.

Although the embodiments show only polyaxial screws as bone anchoring elements, it is conceivable to provide the guides for the connection rods also in the receiving parts of monoaxial bone screws. However, a dynamic stabilization usually requires the use of polyaxial bone anchoring elements.

In use, first, at least two polyaxial bone anchoring elements are anchored in adjacent vertebral bodies or bone parts. Thereafter, the connection rods are inserted into the guides of the polyaxial bone anchoring elements for aligning the receiving parts with respect to each other in an axial direction. If bone anchoring elements are used which have guides for the connection rods in the form of recesses instead of the through holes the connection rods can be clipped into the recesses by inserting them in the U-shaped channel. This facilitates the step of connecting the bone anchoring elements. Then, the flexible rod is inserted. After insertion of the flexible rod the position and the distance of the bone anchoring elements from each other is adjusted. Finally the flexible rod is fixed by tightening the fixation element.

During movements of the motion segments of the spinal column the connection rods 3 can slide within the guides. The connection rods provide resistance against torsional and/or shearing and/or bending forces acting on the stabilization device.

While a particular form of the disclosure has been illustrated and described, it will be apparent that various modifications can be made without departing from the spirit and scope of the disclosure. Accordingly, it is not intended that the disclosure be limited, except as by the appended claims.

What is claimed is:

1. A bone anchoring element comprising:
    an anchoring section for anchoring to a bone;
    a receiving part configured to be pivotably connected to the anchoring section, the receiving part having a first end, a second end, and a generally U-shaped channel extending from the first end towards the second end and forming two legs, wherein each leg has a first side and a second side opposite to the first side along a longitudinal axis of the channel; and
a locking element configured to engage the legs;
wherein the bone anchoring element is adjustable from a first position where the anchoring section and the receiving part are pivotable relative to one another to a second position where an angular orientation between the anchoring section and the receiving part is locked;
wherein each leg defines a substantially straight opening parallel to the longitudinal axis that extends unobstructedly from the first side of the leg to the second side of the leg when the bone anchoring element is at the second position for guiding a connection rod therethrough;
wherein each of the openings is defined by a first portion of the corresponding leg that is directed towards the first end of the receiving part and a second portion of the corresponding leg that is directed towards the second end of the receiving part to restrict movement of an inserted connection rod toward the first and second ends; and
wherein the openings are open to the channel.

2. The bone anchoring element of claim 1, further comprising a securing structure configured to prevent removal of an inserted connection rod from one of the openings.

3. The bone anchoring element of claim 1, wherein the openings are integrally formed in the legs.

4. The bone anchoring element of claim 1, wherein the openings are smaller than an opening defined by free ends of the legs of the receiving part.

5. The bone anchoring element of claim 1, wherein the anchoring section and the receiving part form a polyaxial bone screw.

6. A stabilization system for bones or a spinal column, comprising:
two connection rods; and
two bone anchoring elements, each bone anchoring element comprising:
an anchoring section for anchoring to a bone;
a receiving part configured to be pivotably connected to the anchoring section, the receiving part having a first end, a second end, and a generally U-shaped channel extending from the first end towards the second end and forming two legs, wherein each leg has a first side, a second side opposite to the first side along a longitudinal axis of the channel, and an opening that is parallel to the longitudinal axis and that extends through the leg from the first side of the leg to the second side of the leg; and
a locking element configured to engage the legs to lock an angular orientation between the anchoring section and the receiving part;
wherein each connection rod is configured to be guided through the opening of a corresponding one of the legs of each of the bone anchoring elements to connect the bone anchoring elements to one another.

7. The stabilization system of claim 6, wherein the two connection rods are connectable to each other at one end.

8. The stabilization system of claim 6, further comprising a stabilization rod receivable in the channel, wherein a diameter of each of the connection rods is smaller than a diameter of the stabilization rod.

9. The stabilization system of claim 8, wherein for each bone anchoring element, the locking element is moveable from an unlocked position wherein the stabilization rod is freely movable in the channel to a locked position wherein the stabilization rod is fixed in the channel with the locking element, and wherein the connection rods are freely moveable in the openings in both the unlocked and the locked positions.

10. The stabilization device of claim 6, wherein the two bone anchoring elements comprise polyaxial bone screws, and wherein the connection rods align the receiving parts of the polyaxial bone screws when the connection rods are guided in the openings of the bone anchoring elements.

11. The stabilization system of claim 6, wherein the connection rods are entirely spaced apart in the bone anchoring elements.

12. A method of attaching a stabilization device to bone or vertebra, the stabilization device comprising two connection rods and two bone anchoring elements, each bone anchoring element comprising an anchoring section for anchoring to a bone, a receiving part configured to be pivotably connected to the anchoring section, the receiving part having a first end, a second end, and a generally U-shaped channel extending from the first end towards the second end and forming two legs, wherein each leg has a first side, a second side opposite to the first side along a longitudinal axis of the channel, and an opening that is parallel to the longitudinal axis and that extends through the leg from the first side of the leg to the second side of the leg, and a locking element configured to engage the legs to lock an angular orientation between the anchoring section and the receiving part, the method comprising:
anchoring the anchoring sections of the bone anchoring elements to bone or vertebra;
adjusting respective angular orientations of each of the receiving parts relative to the corresponding anchoring section;
guiding the connection rods through corresponding ones of the openings in the legs of each receiving part; and
inserting respective locking elements in the corresponding receiving part to lock the angular orientation between the receiving part and the corresponding anchoring section.

13. The method of claim 12, further comprising inserting a stabilization rod in the channel of each receiving part.

14. The method of claim 13, wherein the connection rods are guided through the openings of the legs of each receiving part before inserting the stabilization rod in the channel of each receiving part.

15. The method of claim 13, further comprising moving the locking element of each bone anchoring element from an unlocked position wherein the stabilization rod is freely movable in the channel of each receiving part, to a locked position wherein the stabilization rod is fixed in the channel of each receiving part, and wherein the connection rods are freely moveable in the openings in both the unlocked and the locked positions.

* * * * *

UNITED STATES PATENT AND TRADEMARK OFFICE
CERTIFICATE OF CORRECTION

PATENT NO. : 9,907,578 B2
APPLICATION NO. : 14/798072
DATED : March 6, 2018
INVENTOR(S) : Lutz Biedermann et al.

It is certified that error appears in the above-identified patent and that said Letters Patent is hereby corrected as shown below:

In the Claims

Column 8, Line 12, Claim 10, delete "device" and insert -- system --

Signed and Sealed this
Fourteenth Day of May, 2019

Andrei Iancu
*Director of the United States Patent and Trademark Office*